US007983427B2

(12) United States Patent
Yamkovoy et al.

(10) Patent No.: US 7,983,427 B2
(45) Date of Patent: Jul. 19, 2011

(54) METHOD AND APPARATUS FOR CONSERVING BATTERY POWER

(75) Inventors: Paul G. Yamkovoy, Acton, MA (US); Daniel M. Gauger, Jr., Cambridge, MA (US)

(73) Assignee: Bose Corporation, Framingham, MA (US)

(*) Notice: Subject to any disclaimer, the term of this patent is extended or adjusted under 35 U.S.C. 154(b) by 1193 days.

(21) Appl. No.: 11/673,953

(22) Filed: Feb. 12, 2007

(65) Prior Publication Data

US 2008/0192942 A1 Aug. 14, 2008

(51) Int. Cl.
*H04R 1/10* (2006.01)
*A61F 11/06* (2006.01)

(52) U.S. Cl. ......... 381/74; 381/72; 381/71.6; 455/575.2

(58) Field of Classification Search .................... 381/72, 381/74, 58, 59, 71.6, 111–117, 120, 123, 381/124; 455/90.2, 569.1, 575.2; 379/430
See application file for complete search history.

(56) References Cited

U.S. PATENT DOCUMENTS

| | | | | |
|---|---|---|---|---|
| 2,797,315 | A | | 6/1957 | Hoist |
| 3,862,379 | A | | 1/1975 | Pless |
| 4,010,340 | A | | 3/1977 | Palmaer |
| 4,677,678 | A | | 6/1987 | McCutchen |
| 4,899,388 | A | | 2/1990 | Mlodzikowski et al. |
| 5,144,678 | A | | 9/1992 | Lenz |
| 5,212,811 | A | | 5/1993 | Kuge et al. |
| 5,218,641 | A | | 6/1993 | Abe et al. |
| 5,353,347 | A | | 10/1994 | Irissou et al. |
| 5,396,551 | A | * | 3/1995 | Lucey ........................... 379/395 |
| 5,557,653 | A | * | 9/1996 | Paterson et al. ............ 455/575.2 |
| 5,708,725 | A | | 1/1998 | Ito |
| 6,118,878 | A | | 9/2000 | Jones |
| 6,704,428 | B1 | | 3/2004 | Wurtz |
| 6,856,046 | B1 | | 2/2005 | Scarlett |
| 6,988,905 | B2 | | 1/2006 | Corey et al. |
| 7,010,332 | B1 | | 3/2006 | Irvin et al. |
| 7,103,188 | B1 | | 9/2006 | Jones |
| 7,327,850 | B2 | * | 2/2008 | Crump et al. ................... 381/74 |
| 7,418,103 | B2 | * | 8/2008 | Sargaison ....................... 381/74 |
| 7,668,308 | B1 | * | 2/2010 | Wurtz ........................... 379/430 |
| 7,945,297 | B2 | * | 5/2011 | Philipp ...................... 455/575.2 |
| 2005/0053243 | A1 | | 3/2005 | Ganton |
| 2005/0201568 | A1 | | 9/2005 | Goyal |

(Continued)

FOREIGN PATENT DOCUMENTS

JP 03-123199 5/1991

(Continued)

OTHER PUBLICATIONS http://playlistmag.com/products/complete/383-0detail.php, Altec Lansing inMotion iM11, pp. 1-4, downloaded Jan. 26, 2007.

(Continued)

*Primary Examiner* — Xu Mei

(57) ABSTRACT

A method of conserving battery power includes providing an electrical conductor that is connectable between an audio source and an accessory of the audio source. The conductor is capable of conducting a first electrical signal, containing audio information from the audio source, to the accessory. A second electrical signal is applied to the conductor when the first electrical signal is not present on the conductor. An aspect of the second electrical signal is measured while it is being applied to the conductor. An amount of battery power supplied to the accessory is reduced when the measured aspect meets a predetermined condition.

51 Claims, 4 Drawing Sheets

U.S. PATENT DOCUMENTS

2007/0121959 A1* 5/2007 Philipp .......................... 381/74

FOREIGN PATENT DOCUMENTS

| | | |
|---|---|---|
| WO | WO 99/14982 | 3/1999 |
| WO | WO 2006/006910 | 1/2006 |
| WO | 2007016020 | 2/2007 |

OTHER PUBLICATIONS

Sony TCM-200DV Cassette Recorder with Dual Power Source, Amazon.com, http://www.amazon.com/Sony-TCM-200DV-Cassette-Recorder-Source/dp/B00008WIX3, downloaded Feb. 21, 2007.

Dallas Semiconductor Maxim, AutoShutdown for Speaker Amplifier Conserves Cellphone Power, Application Note 3612, http://www.maxim-ic.com/appnotes.cfm/an_pk/3612, Aug. 26, 2005.

International Preliminary Report on Patentability dated Aug. 27, 2009 for PCT/US2008/053698.

International Search Report and Writen Opinion dated Nov. 13, 2008, issued in International Application No. PCT/US2008/053698, filed Feb. 12, 2008.

* cited by examiner

METHOD AND APPARATUS FOR CONSERVING BATTERY POWER

TECHNICAL FIELD

The present invention concerns methods and apparatus for conserving battery power in an accessory such as battery powered headphones or headsets with automatic noise-reduction circuitry or other active electronics on-board.

BACKGROUND OF THE INVENTION

A battery powered accessory, such as a headset, can be connected to an audio source (e.g. an aviation intercom). The battery powers electronics in the headset such as active noise reduction circuitry. It is important not to waste battery power when the headset is disconnected from the intercom or when the intercom is powered down.

SUMMARY OF THE INVENTION

A method of conserving battery power includes providing an electrical conductor that is connectable between an audio source and an accessory of the audio source. The conductor is capable of conducting a first electrical signal, containing audio information from the audio source, to the accessory. A second electrical signal is applied to the conductor when the first electrical signal is not present on the conductor. An aspect of the second electrical signal is measured while it is being applied to the conductor. An amount of battery power supplied to the accessory is reduced when the measured aspect meets a predetermined condition.

According to other aspects of the invention, the reducing step can be effective to reduce battery power supplied to the accessory such that an active noise cancellation system of the accessory is shut off. The audio source can be an aviation intercom system. The accessory can be a headset. The headset can include an active noise cancellation system that uses battery power. The headset can include a microphone. The aspect that is measured can be related to an output impedance of the audio source. When the predetermined condition is met it can indicate that an output impedance of the audio source is about ≧500 Ohm. The applying step can include a step of injecting an electrical current into the electrical conductor, and a step of measuring a voltage on the electrical conductor. The reducing step can be effective to reduce battery power supplied to the accessory such that the accessory is put in a standby state.

Further aspects of the invention include the feature wherein prior to the applying step, an impedance is increased between a source of the second electrical signal and the accessory. The impedance can be increased by opening a switch between the source of the second electrical signal and the accessory. The reducing step can be effective to reduce battery power supplied to the accessory such that circuitry in the accessory is shut off. When the measured aspect meets the predetermined condition and the audio source is connected to the accessory by the electrical conductor, it can indicate that the electrical conductor is not connected to the audio source. When the measured aspect meets the predetermined condition it can indicate that the audio source is powered off. The applying step may not be done if the first electrical signal is detected on the electrical conductor. The reducing step can be delayed by a period of time after the measuring step. A user of the accessory can disable the reducing step. The accessory can be capable of producing sound up to an upper frequency cutoff point, the second electrical signal having a frequency that is about at or above this cutoff point.

BRIEF DESCRIPTION OF THE DRAWINGS

This invention is described with particularity in the detailed description. The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Embodiments below describe controlling the operational state of a battery powered headset or other accessory depending on (a) the state of the connection of the headset with an external audio source such as an aviation intercom, and (b) whether or not the intercom is powered up. This can be done by sensing a voltage on the connection when a known electrical current is injected into the connection. When the measured voltage meets a predetermined condition, indicating the headset is not connected to the intercom or the intercom is powered off, battery power to the headset is reduced to conserve battery power. The headset can be placed in a standby or sleep mode by reducing the battery output power to a low level. Standby mode allows the headset to quickly "wake up" when necessary. Alternatively, the battery power can be reduced to zero which turns the headset completely off.

Figure 1:
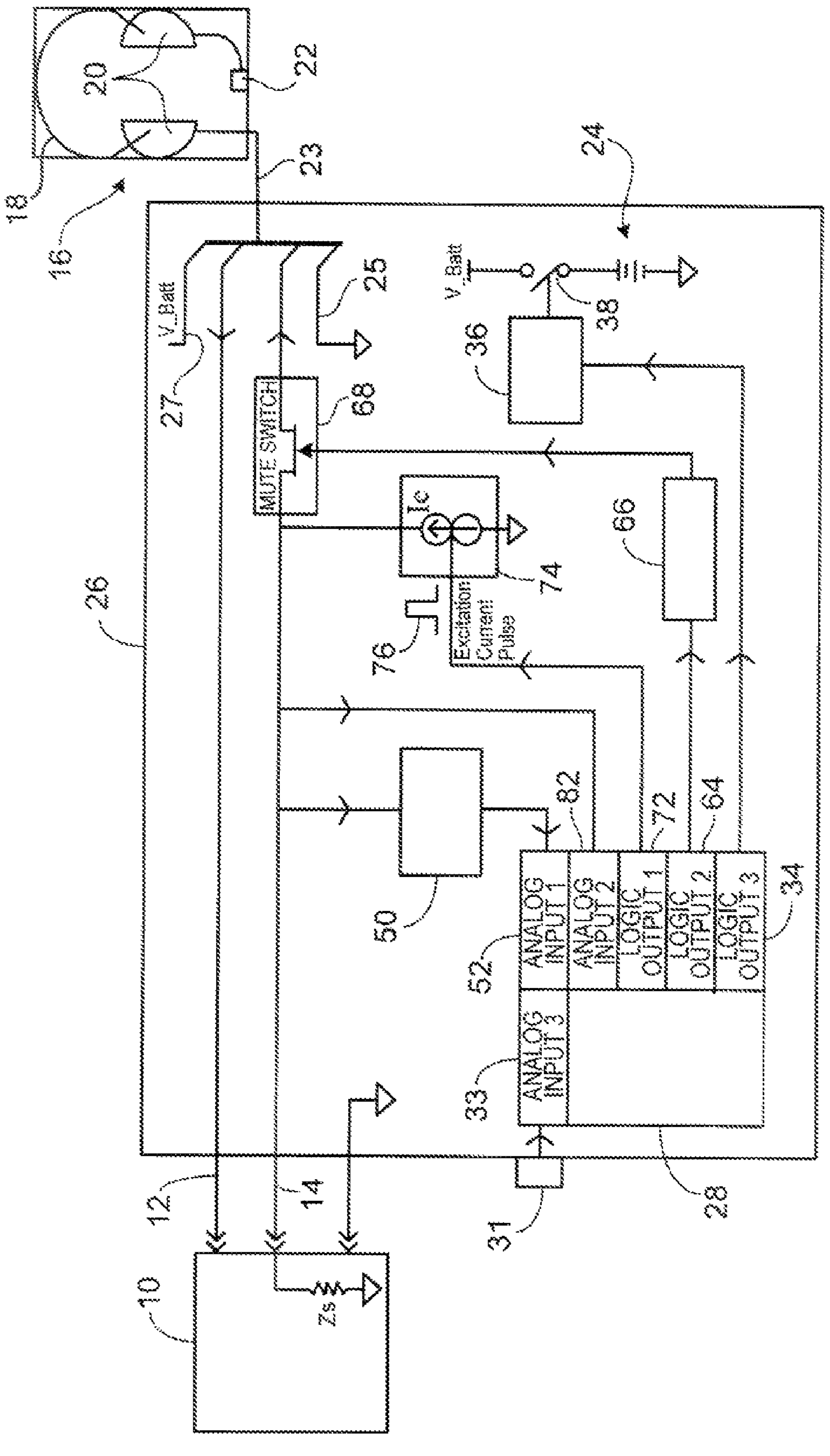
FIG. 1 is an apparatus for conserving battery power in a battery operated accessory which is connectable to an audio source via an electrical conductor.

With reference to FIG. 1, an audio source 10 in this embodiment is an aviation intercom system that pilots use to communicate with, for example, each other and ground control. Audio source 10 can alternatively be a cell phone, MP3 player, CD player, portable DVD player or any other source of audio signals. These other types of audio sources can be powered with batteries, a vehicle electrical system, or a conventional household electrical system. Intercom 10 is electrically powered by the airplane in which it resides. An electrical conductor 12 and an electrical conductor 14 electrically couple intercom 10 with other elements including an accessory 16. Conductor 14 is capable of conducting a first electrical signal, containing audio information from the intercom 10, to the accessory. Intercom 10 has an output impedance and provides an electrical load on conductor 14. Accessory 16 in this embodiment is an aviation headset which includes a band 18, two earcups 20 and a microphone 22. Accessory 16 can alternatively be a powered speaker or other device that uses battery power and receives audio signals. Each earcup 20 includes a speaker (not shown) for transmitting audio information to the wearer of headset 16. Active noise reduction (ANR) circuitry (not shown) is also part of the headset and is preferably located in one or both of earcups 20. As is well known to those skilled in the art, the ANR circuitry causes the speakers to output an acoustic signal which approximates the ambient noise present in the vicinity of headset 16, the output acoustic signal having approximately opposite polarity and equal amplitude compared to the noise signal. This has the effect of canceling the ambient noise within earcups 16.

An electrical conductor 23 from headset 16 enters into a battery and control module 26. Conductor 23 actually includes four separate electrical conductors which are shown within module 26. A first one of these conductors is conductor 12 (described above) through which audio information is transmitted from microphone 22 to intercom 10. In this embodiment conductor 12 passes through module 26 without any electrically interfacing with any components in the module. A second one of these conductors is conductor 14 (described above) through which audio information is transmitted from intercom (audio source) 10 to headset 16. A third one of these conductor is a common conductor 25 (ground). A fourth one of these conductors is conductor 27 through which electrical power from a battery 24 is supplied to the ANR circuitry in headset 16. In this embodiment battery and control module 26 is shown as a separate component from intercom 10 and headset 16. It should be noted that some or all of the components in module 16 can alternatively be included in intercom 10 and/or headset 16.

Figure 2:
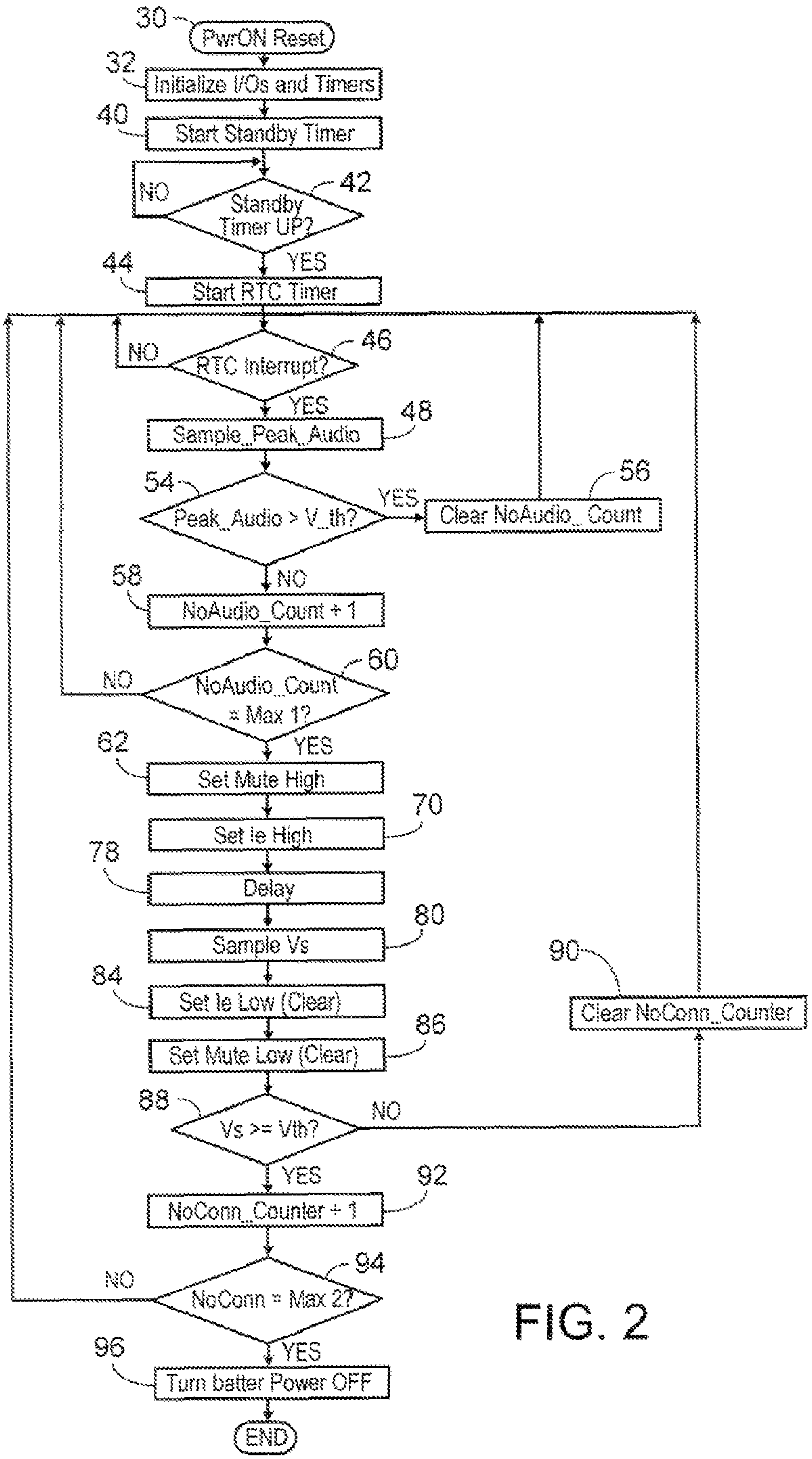
FIG. 2 is a flow chart representing an algorithm that is used in a micro-controller of FIG. 1.

Referring now to FIGS. 1 and 2, a micro-controller 28 controls operation of module 26. The flow chart shown in FIG. 2 represents an algorithm that is run by micro-controller 28. An overview of how this algorithm operates is as follows. The micro-controller detects when a power button 31 is pressed to turn on module 26. When module 26 is turned on, battery power is immediately supplied to headset 16. This arrangement provides the user with ANR even if lines 12 and 14 have not yet been plugged into intercom 10, and if intercom 10 is not yet powered up. The algorithm waits a period of time to allow the electronics in module 26 to settle, the headset user to plug into intercom 10, and the user to power up the intercom. The algorithm then checks to see if a first electrical signal containing audio information from the audio source is being transmitted from the audio source to the headset on an electrical conductor. When no such first electrical signal is detected on the conductor for a set time period, a second electrical signal is injected into the electrical conductor. An aspect of the second electrical signal such as voltage on the conductor is measured. If the measured voltage is at or above a predetermined level, this indicates that the intercom is powered off or that the headset is disconnected from the intercom. In this case, battery power to the headset is reduced, preferably to zero, to conserve battery power. A particular operation of one embodiment is described in more detail below.

In a block 30 the logic detects that a user of the module and headset 16 has turned on the module by pressing switch 31. The signal from the switch is passed into the micro-controller by an analog input 3 identified by a reference numeral 33. At a block 32 the logic initializes all inputs and outputs to an initial function, and sets all timers to zero. This includes having a logic output 3, identified by reference numeral 34, instruct a battery switch control 36 to close a switch 38 if it is not already closed. As such, battery power is supplied to the ANR or other active circuitry in headset 16. At a block 40 the logic starts a standby timer and at a block 42 it is determined whether the standby time is up. In this embodiment the standby time is preferably 3 minutes. The standby time gives the circuitry time to settle and also allows time for the user to plug headset 16 into intercom 10 and turn on the intercom power.

When the standby time has expired, a real time clock (RTC) is started at a logic block 44. At a block 46 the logic determines whether or not an RTC interrupt has occurred. In this embodiment an RTC interrupt is generated about every 1.2 seconds. Once an RTC interrupt is generated, a logic block 48 causes microcontroller 28 to sample the peak audio signal on conductor 14. The peak audio signal is detected by an amplitude detector 50 which measures a voltage on conductor 14. The measured voltage is passed into the microcontroller via an analog input 1 identified by reference numeral 52. At a logic block 54 it is checked whether or not the peak audio is greater than Vth. In this embodiment Vth is preferably about 50 mV. When Vth is greater than 50 mV it indicates the presence of an audio signal on conductor 14 and a logic block 56 sets "No Audio Count" to zero and returns to block 46. When Vth is not greater than 50 mV a logic block 58 sets "No Audio Count"="No Audio Count"+1. At a logic block 60 it is checked whether "No Audio Count"=Max1. In this embodiment Max1 is preferably set at 10. When "No Audio Count" has not reached Max1 the logic returns to block 46. When "No Audio Count" has reached Max1 the logic proceeds to a logic block 62. The logic described in this paragraph determines whether or not there has been no substantial audio signal on conductor 14 for about 12 seconds. If there is an audio signal (electrical signal greater than 50 mV) on conductor 14 within about 12 seconds the subroutine does not proceed further.

At logic block 62 a "Mute" output is set to high by microcontroller 28 through a logic output 2 identified by reference numeral 64. A level converter 6 converts the 2.7 volt signal from logic output 2 into a −6 volt signal which causes a mute switch 68 (preferably a J Fet transistor) to open. The result is an increase in impedance between an electrical current source 74 and headset 16. This temporarily hinders any first electrical signals from intercom 10 and an excitation current pulse (second electrical signal) from current source 74 (explained further below) from reaching the speakers in earcups 20 of headset 16. At a logic block 70 Ie is set to high which is output as a 2.7 volt signal at a logic output 1 identified by a reference numeral 72. Electrical current source 74 converts the 2.7 volt signal into a square pulse of electrical current (see element 76) which is injected into conductor 14. The current pulse is preferably at about 100 uA. At a logic block 78 a time delay of preferably about 200 uS occurs to allow the circuit to settle. At a logic block 80 a voltage Vs on conductor 14 is sampled (measured) and input into microcontroller 28 via an analog input 2 identified by a reference numeral 82. At a logic block 84 Ie is set to low which causes current source 74 to stop injecting electrical current into conductor 14. At a logic block 86 the "Mute" output is set to low which causes mute switch 68 to close. Mute switch 68 is opened is so that a wearer of headset 16 does not hear an audible noise (e.g. click) when the current pulse is injected into conductor 14.

The measured voltage in block 80 is related to an impedance Z of conductor 14. This impedance may or may not include an output impedance of a powered up or powered down intercom 10 depending on whether or not conductor 14 is connected to intercom 10. We are thus determining an electrical characteristic of conductor 14. Impedance is calculated as Z=V/Ie. By knowing the impedance we can determine (a) whether or not conductor 14 is connected to intercom 10, and (b) whether or not intercom 10 is powered up when conductor 14 is connected to the intercom. When conductor 14 is not connected to intercom 10, the sampled voltage is about 2.7 volts (the maximum voltage from current source 74 into the open circuit). A measured voltage of about 2.7 volts indicates an infinite impedance. When conductor 14 is connected to an unpowered intercom 10, the sampled voltage is about 50 mV. With an Ie of 100 uA this yields an output impedance of intercom 10 of about 500 Ohm. Finally, when conductor 14 is connected to an electrically powered intercom 10, the sampled voltage is below about 5 mV. With an Ie of 100 uA this yields an impedance of below about 50 Ohm.

When conductor 14 is connected to a powered down intercom or disconnected from the intercom for a set period of time, switch 38 will be opened to shut off the ANR active electronics and conserve battery power. This will be explained further below.

At a logic block 88 it is checked whether Vs≧Vth. In this embodiment Vth is preferably about 50 mV. When this predetermined condition is not met a "NoConn Counter" (i.e. no connection or connected to unpowered intercom) is set to zero at a block 90 and the logic returns to a block 46. When the predetermined condition is met "NoConn Counter" value is increased by 1 at a logic block 92. When Vs≧50 mV it indicates that either (a) conductor 14 is not connected to intercom 10, or (b) conductor 14 is connected to a powered down intercom 10. At a logic block 94 it is checked whether "NoConn Counter"=Max2. If this condition is not met the logic cycles back to block 46. If this condition is met the logic proceeds to a block 96 where microcontroller 28 instructs switch control 36 via logic output 3 to open switch 38. In this embodiment, battery power from battery 24 to headset 16 is reduced to zero, thereby shutting of the ANR circuitry. Alternatively, the battery power can be reduced to a lower level above zero such that the headset is put into a standby or sleep mode. Being in standby mode allows headset 16 to "wake up" quicker. The operating state of the headset is thus adjusted automatically. The operating state of the headset can be adjusted by (a) reducing battery power to the headset, (b) turning off the battery power to the headset, (c) placing the headset in a standby or sleep mode, and (d) altering another electrical aspect of the headset. Max2 here is chosen so that preferably about 3 minutes of time must elapse with substantially no audio signal on conductor 14 and, intercom 10 being powered down or conductor 14 disconnected from intercom 10, before switch 38 is opened. Since RTC timer generates an interrupt every 1.2 seconds, Max2 can preferably be about 150. The subroutine of FIG. 2 ends at a logic block 98.

Figure 3:
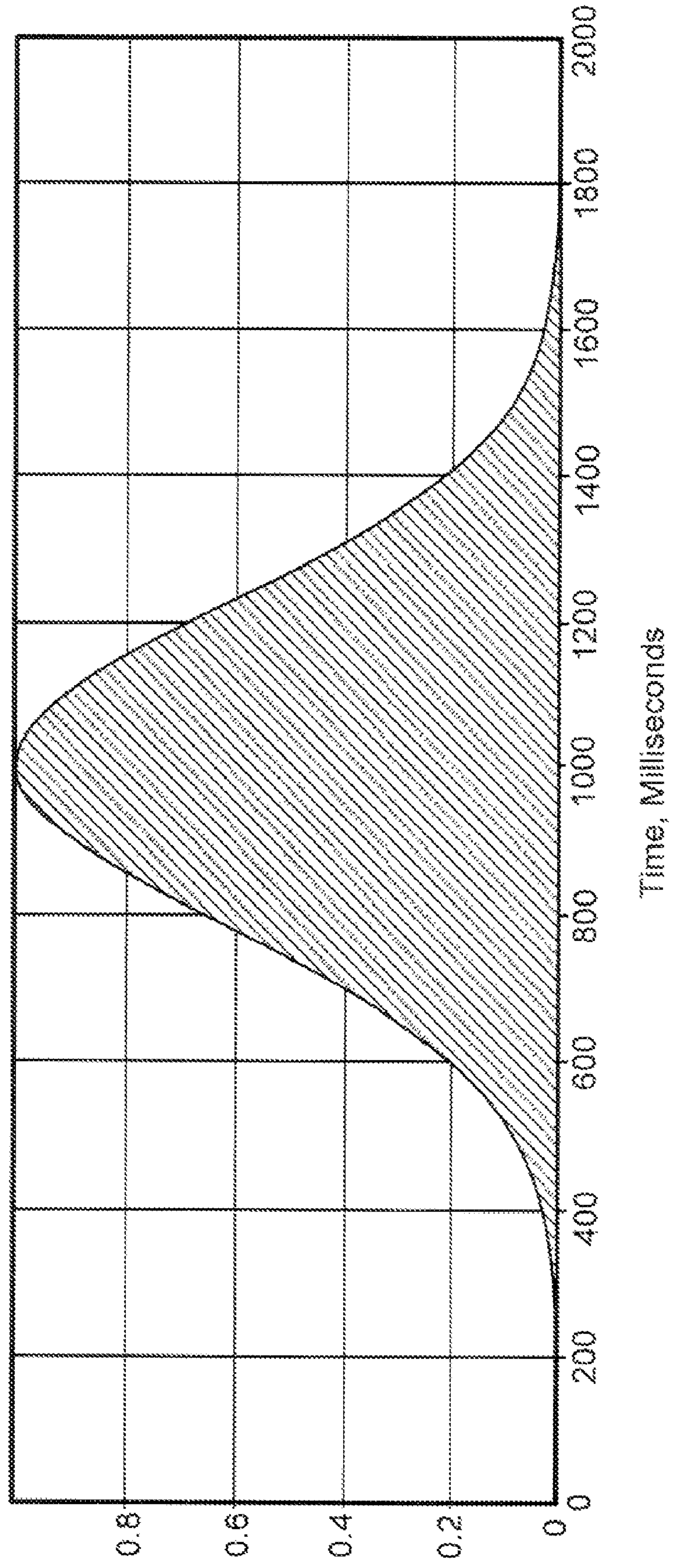
FIG. 3 discloses an excitation current waveform that can be used in the apparatus of FIG. 1.
Figure 4:
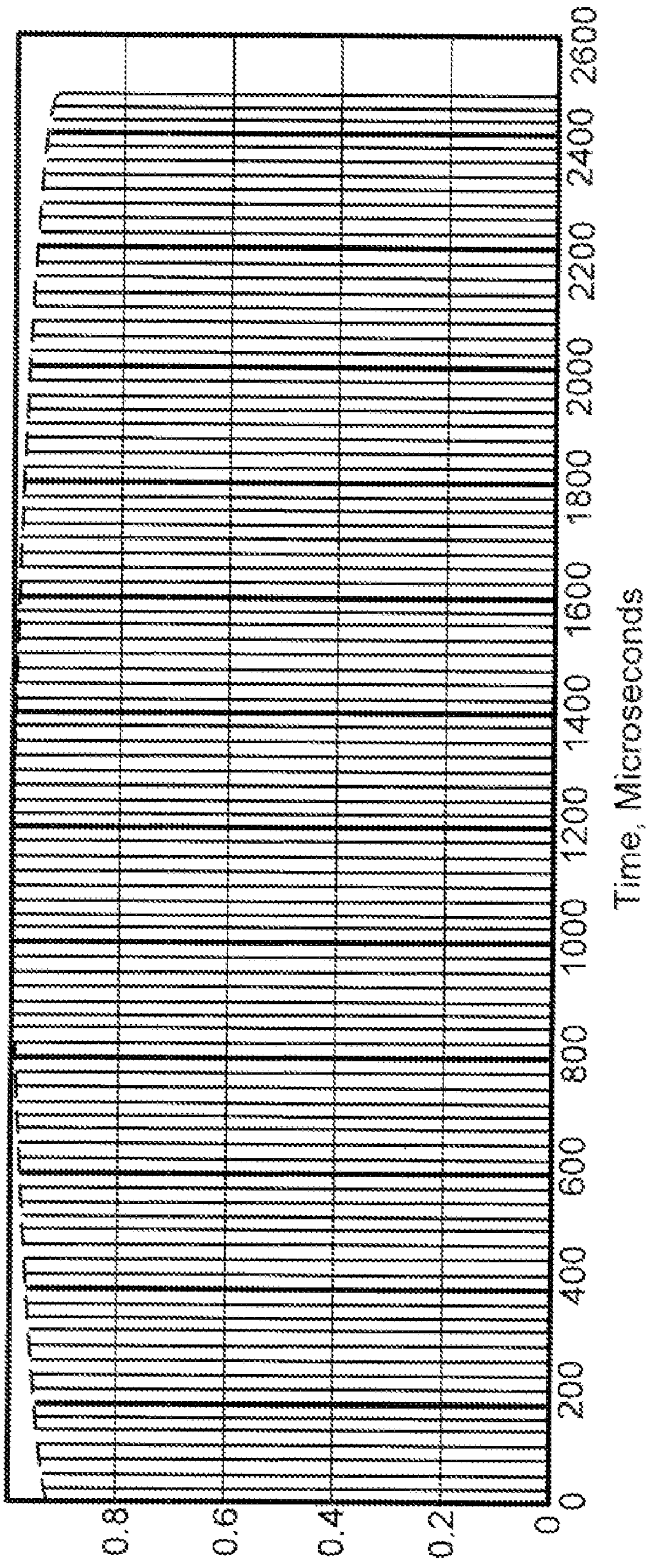
FIG. 4 discloses a portion of the excitation current waveform of FIG. 3.

Turning now to FIGS. 3 and 4, an alternate current pulse will be discussed that can be used in place of the square pulse described above. In FIG. 3 it can be seen that the duration of the pulse is preferably about 1.6 seconds. The shape of this pulse is similar to a bell shaped curve. FIG. 4 shows a small piece of FIG. 3 near the 1000 millisecond portion of the curve and near the top of the curve. The signal is preferably an AC signal having a frequency that is above an upper frequency cutoff point of the headset. This cutoff point represents the highest frequency audio signal that can be reproduced by the speakers in headset 16. For example, the upper frequency cutoff point of headset 16 might be 15 kHz. FIG. 3 shows that in this embodiment the signal is made up of a large number of square pulses that are occurring at preferably about 22 kHz (above the audible range). This signal allows mute switch 68 (FIG. 1) to be eliminated because the signal cannot be heard by a wearer of headset 16 even if mute switch 68 is closed. Further, because an impedance of headset 16 (about 4.7 kOhm) is much higher than the impedance of intercom 10, most of the second electrical signal current pulse will travel into intercom 10 when conductor 14 is plugged into the intercom. As an alternative to the square pulses shown in FIG. 4, the signal can be in the form of a sine wave. A still further alternative of the signal involves having the signal alternate between positive and negative current during each cycle of the signal.

In an alternative embodiment of the invention, a user of the intercom and headset can disable the auto-off feature by, for example, pressing switch 31 for a set period of time (e.g. 3 seconds) when turning on the module. This action causes the microcontroller to ignore the logic sequence shown in FIG. 2. When the user presses switch 31 again to shut off the module, the disable feature is also shut off.

In another embodiment of the invention, current source 74 is replaced with a constant voltage source, and the current on conductor 14 is measured instead of the voltage. Alternatively, the current source can be replaced by an electrical source that does not output a constant voltage or current. In this case both current and voltage are measured on conductor 14 to determine if the predetermined condition is met.

What is claimed is:

1. A method of conserving battery power, comprising the steps of:
- providing an electrical conductor that is connectable between an audio source and an accessory of the audio source, the conductor capable of conducting a first electrical signal, containing audio information from the audio source, to the accessory;
- applying a second electrical signal to the conductor when the first electrical signal is not present on the conductor;
- measuring an aspect of the second electrical signal which it is being applied to the conductor; and
- reducing an amount of battery power supplied to the accessory when the measured aspect meets a predetermined condition.

2. The method of claim 1, wherein the reducing step is effective to reduce battery power supplied to the accessory such that an active noise cancellation system of the accessory is shut off.

3. The method of claim 1, wherein the audio source is an aviation intercom system.

4. The method of claim 1, wherein the accessory is a headset.

5. The method of claim 4, wherein the headset includes an active noise cancellation system that uses battery power.

6. The method of claim 4, wherein the headset includes a microphone.

7. The method of claim 1, wherein the aspect that is measured is related to an output impedance of the audio source.

8. The method of claim 1, wherein when the predetermined condition is met it indicates that an output impedance of the audio source is about ≧500 Ohm.

9. The method of claim 1, wherein the applying step includes a step of injecting an electrical current into the electrical conductor, and a step of measuring a voltage on the electrical conductor.

10. The method of claim 1, wherein prior to the applying step, an impedance is increased between a source of the second electrical signal and the accessory.

11. The method of claim 10, wherein the impedance is increased by opening a switch between the source of the second electrical signal and the accessory.

12. The method of claim 1, wherein the reducing step is effective to reduce battery power supplied to the accessory such that the accessory is put in a standby state.

13. The method of claim 1, wherein when the measured aspect meets the predetermined condition it indicates that the electrical conductor is not connected to the audio source.

14. The method of claim 1, wherein when the measured aspect meets the predetermined condition and the audio source is connected to the accessory by the electrical conductor, it indicates that the audio source is powered off.

15. The method of claim 1, wherein the applying step is not done if the first electrical signal is detected on the electrical conductor.

16. The method of claim 1, wherein the reducing step is delayed by a period of time after the measuring step.

17. The method of claim 1, wherein a user of the accessory can disable the reducing step.

18. The method of claim 1, wherein the accessory is capable of producing sound up to an upper frequency cutoff point, the second electrical signal having a frequency that is about at or above this cutoff point.

19. The method of claim 1, wherein the reducing step is effective to reduce battery power supplied to the accessory such that circuitry in the accessory is shut off.

20. The method of claim 1, wherein the second electrical signal does not contain audio information from the audio source.

21. An apparatus for conserving battery power in a battery operated accessory which is connectable to an audio source via an electrical conductor, the conductor capable of conducting a first electrical signal, containing audio information from the audio source, to the accessory, comprising:

an electrical signal source that is capable of injecting a second electrical signal into the conductor when the first electrical signal is not present on the conductor;

a measurement device that measures an aspect of the second electrical signal while the electrical signal source is injecting the second electrical signal into the conductor; and a logic device for determining whether or not the measured aspect meets a predetermined condition, the logic device reducing an amount of battery power supplied to the accessory when the predetermined condition is met.

22. The apparatus of claim 21, wherein the battery power supplied to the accessory is reduced such that an active noise cancellation system of the accessory is shut off.

23. The apparatus of claim 21, wherein the audio source is an aviation intercom system.

24. The apparatus of claim 21, wherein the accessory is a headset.

25. The apparatus of claim 24, wherein the headset includes an active noise cancellation system that uses battery power.

26. The apparatus of claim 24, wherein the headset includes a microphone.

27. The apparatus of claim 21, wherein the aspect that is measured is related to an output impedance of the audio source.

28. The apparatus of claim 27, wherein the output impedance is about ≧500 Ohm.

29. The apparatus of claim 21, wherein prior to injecting the second electrical signal into the electrical conductor, an impedance is increased between the source of the second electrical signal and the accessory.

30. The apparatus of claim 21, wherein when the measured aspect meets the predetermined condition it indicates that the electrical conductor is not connected to the audio source.

31. The apparatus of claim 21, wherein when the measured aspect meets the predetermined condition and the audio source is connected to the accessory by the electrical conductor, it indicates that the audio source is powered off.

32. The apparatus of claim 21, wherein the second electrical signal is not injected into the electrical conductor if the first electrical signal is detected on the electrical conductor.

33. The apparatus of claim 21, wherein the logic device delays reducing the battery power for a period of time after the predetermined condition is met.

34. The apparatus of claim 21, wherein a user of the accessory can disable the logic device from reducing the battery power.

35. The apparatus of claim 21, wherein the accessory is capable of producing sound up to an upper frequency cutoff point, the second electrical signal having a frequency that is about at or above this cutoff point.

36. A method of conserving battery power, comprising the steps of:

providing an electrical conductor that is connectable between an audio source and an accessory of the audio source, the conductor capable of conducting a first electrical signal, containing audio information from the audio source, to the accessory;

applying a second electrical signal to the conductor when the first electrical signal is not present on the conductor measuring an aspect of the second electrical signal while it is being applied to the conductor; and adjusting an operating state of the accessory when the measured aspect meets a predetermined condition.

37. The method of claim 36, wherein the adjusting step is effective to shut off an active noise cancellation system of the accessory.

38. The method of claim 36, wherein the audio source is an aviation intercom system.

39. The method of claim 36, wherein the accessory is a headset.

40. The method of claim 39, wherein the headset includes an active noise cancellation system that uses battery power.

41. The method of claim 39, wherein the headset includes a microphone.

42. The method of claim 36, wherein the aspect that is measured is related to an output impedance of the audio source.

43. The method of claim 42, wherein the output impedance is about ≧500 Ohm.

44. The method of claim 36, wherein the applying step includes a step of injecting an electrical current into the electrical conductor, and a step of measuring a voltage on the electrical conductor.

45. The method of claim 36, wherein prior to the applying step, an impedance is increased between a source of the second electrical signal and the accessory.

46. The method of claim 36, wherein when the measured aspect meets the predetermined condition it indicates that the electrical conductor is not connected to the audio source.

47. The method of claim 36, wherein when the measured aspect meets the predetermined condition and the audio source is connected to the accessory by the electrical conductor, it indicates that the audio source is powered off.

48. The method of claim 36, wherein the applying step is done if the first electrical signal is detected on the electrical conductor.

49. The method of claim 36, wherein the adjusting step is delayed by a period of time after the measuring step.

50. The method of claim 36, wherein a user of the accessory can disable the adjusting step.

51. The method of claim 36, wherein the accessory is capable of producing sound up to an upper frequency cutoff point, the second electrical signal having a frequency that is about at or above this cutoff point.

* * * * *